United States Patent [19]

Kulprathipanja

[11] Patent Number: 5,849,981
[45] Date of Patent: Dec. 15, 1998

[54] ADSORPTIVE SEPARATION OF PARA-XYLENE USING ISOPROPYLBENZENE DESORBENT

[75] Inventor: Santi Kulprathipanja, Inverness, Ill.

[73] Assignee: UOP LLC, Des Plaines, Ill.

[21] Appl. No.: 882,427

[22] Filed: Jun. 25, 1997

Related U.S. Application Data

[63] Continuation of Ser. No. 638,568, Feb. 20, 1996, abandoned, which is a continuation-in-part of Ser. No. 320,343, Oct. 11, 1994, Pat. No. 5,495,061.

[51] Int. Cl.$^6$ ..................................................... G07C 7/13
[52] U.S. Cl. .......................................... 585/828; 585/831
[58] Field of Search ...................................... 585/828, 831

[56] References Cited

U.S. PATENT DOCUMENTS

| | | | |
|---|---|---|---|
| 3,686,342 | 8/1972 | Neuzil | 260/674 SA |
| 3,734,974 | 5/1973 | Neuzil | 260/674 SA |
| 3,878,127 | 4/1975 | Rosback | 252/455 Z |
| 3,997,620 | 12/1976 | Neuzil | 260/674 SA |
| 4,001,111 | 1/1977 | Geissler et al. | 210/24 |
| 4,029,717 | 6/1977 | Healy et al. | 260/674 SA |
| 4,886,930 | 12/1989 | Zinnen | 585/828 |
| 5,012,038 | 4/1991 | Zinnen | 585/828 |
| 5,057,643 | 10/1991 | Zinnen | 585/828 |
| 5,159,131 | 10/1992 | Zinnen | 585/828 |

*Primary Examiner*—Glenn Caldarola
*Assistant Examiner*—Thuan D. Dang
*Attorney, Agent, or Firm*—Thomas K. McBride; John F. Spears, Jr.

[57] ABSTRACT

The cost of separating para-xylene from other xylene isomers and $C_9$ aromatics by adsorption on zeolitic molecular sieves is reduced by the use of 1,4 diisopropylbenzene as a relatively high boiling desorbent. The desorbent has surprisingly high strength and selectivity characteristics with the preferred desorbent. The preferred adsorbent is an X zeolite containing barium or both barium and potassium ions at exchangeable cationic sites. The para-xylene components are selectively adsorbed onto the adsorbent. The non-adsorbed feed is then removed from the adsorbent and the para-xylene recovered by desorption.

8 Claims, No Drawings

ADSORPTIVE SEPARATION OF PARA-XYLENE USING ISOPROPYLBENZENE DESORBENT

CROSS-REFERENCE TO RELATED APPLICATIONS

This application is a continuation of application Ser. No. 08/638,568 filed 20 Feb., 1996, abandoned, which was a continuation-in-part of application Ser. No. 08/320,343 filed 11 Oct., 1994, now U.S. Pat. No. 5,495,061

FIELD OF THE INVENTION

The subject invention relates to a process for the adsorptive separation of aromatic hydrocarbons. More specifically, the invention relates to a process for separating para-xylene from a feed mixture comprising at least two xylene isomers, including the para-isomer, which process employs a zeolitic adsorbent and a particular desorbent. The invention is particularly advantageous in a process in which the feed contains $C_9$ aromatic hydrocarbons in addition to the xylene isomers.

BACKGROUND OF THE INVENTION

The polyester fabrics which are in wide use today are produced from paraphthalic acid which is in turn produced by the oxidation of para xylene. Para xylene is typically derived from a xylene isomerization zone or from a stream separated from an aromative rich precursor, such as a $C_8$ aromatic hydrocarbon fraction derived from a catalytic reformate by liquid-liquid extraction and fractional distillation. The para xylene is commercially separated from a paraxylene-containing feed stream, usually containing all three xylene isomers, by either crystallization or adsorptive separation or a combination of these two techniques. Adsorptive separation is the newer technique which has captured the great majority of the market share of newly constructed plants for the production of paraxylene.

RELATED ART

U.S. Pat. No. 3,686,342 issued to R. W. Neuzil discloses that para-diethylbenzene (DEB) is a good desorbent for the separation of para xylene from mixed xylenes using an aluminosilicate adsorbent. The use of this desorbent is described as allowing a more efficient separation with a higher purity extract stream being recovered from the process.

U.S. Pat. No. 4,001,111 issued to R. R. Geissler describes an adsorptive separation process with meta and paradiisopropyl benzene being characterized as the preferred desorbents. This process differs from the subject process in several ways including: a) the selective retention of two or more components of the feed (para xylene and, ethyl benzene) on the adsorbent; b) disclosure of only exchanged Y zeolites as the adsorbent; c) the use of gradient elution chromatography affected by a change in desorbent concentration or a change to stronger desorbent; and d) the step of preheating the stronger or more concentrated desorbent to cause temperature waves to flow through the adsorbent bed.

U.S. Pat. No. 4,029,717 issued to F. J. Healy et al. describes a simulated moving bed adsorptive separation process for the recovery of para-xylene from a mixture of xylene isomers. This patent discloses 1,3 (meta) diisopropylbenzene as a desorbent for use with barium or potassium exchanged X or Y zeolites, but does not address such operating variables as the LOI of the adsorbent.

U.S. Pat. No. 4,886,930 issued to H. A. Zinnen disclosed the benefits of using "heavy" desorbents comprising tetralin or tetralin derivatives for separating para-xylene when the feed mixtures contain higher boiling aromatic hydrocarbons, such as $C_9$ aromatics, $C_{10}$ aromatics, etc. However, these materials are not readily available except when synthetically produced. Therefore, it is desirable to find a higher boiling point material, i.e., "heavy desorbent", that meets the selectivity requirements for desorbents which can be used with feed mixtures containing $C_9$ aromatics and is available from natural, rather than synthetic, sources, such as coal tar distillates, etc.

U.S. Pat. No. 5,012,038 issued to H. A. Zinnen addressed the issue of a heavy desorbent for para xylene recovery and disclosed the use of one or a mixture of diethyltoluene isomers, with the 2,3; 2,5 and 2,6 isomers being preferred.

In a similar manner U.S. Pat. No. 5,057,643, also issued to H. A. Zinnen, suggests the use of tetralin or alkyl tetralins as a heavy desorbent for the separation of para xylene from xylene/$C_9$ aromatic hydrocarbon mixtures. in the adsorptive separation of para xylene with x zeolites in U.S. Pat. No. 5,159,131 issued to H. A. Zinnen.

SUMMARY OF THE INVENTION

The invention is the discovery of a new "heavy" desorbent for use in a chromatographic process for separating p-xylene from a feed mixture comprising p-xylene, one or more additional xylene isomers, ethylbenzene and $C_9$ aromatic hydrocarbons. One broad embodiment of the invention may be characterized as a constant temperature process for separating paraxylene from a feed mixture containing paraxylene and at least one other xylene isomer, ethylbenzene and $C_9$ hydrocarbons comprising contacting said feed mixture with an X or Y zeolite having metal cations at exchangeable cationic sites to effect the selective adsorption of p-xylene by the zeolite and producing a raffinate comprising substantially all of the other xylene isomers, ethylbenzene, and $C_9$ aromatics originally present in the feed mixture; and, recovering p-xylene from said adsorbent by contacting the resulting para-xylene loaded adsorbent with a desorbent comprising 1,4 diisopropylbenzene. This desorbent has a higher boiling point than the $C_9$ aromatics, making it possible to separate the $C_9$ aromatics from the desorbent by fractionation so that the desorbent can be reused in the process without building up $C_9$ aromatics in the recycled desorbent. This desorbent also has excellent selectivity and a surprisingly higher strength than its structural analog 1,3 diisopropylbenzene, which provides significant economic advantages in a commercial process unit.

DETAILED DESCRIPTION AND PREFERRED EMBODIMENTS

In numerous processes described in the patent literature zeolitic adsorbents are used to separate the para isomer of dialkyl substituted monocyclic aromatics from the other isomers. The separation of para-xylene from other xylene isomers is both widely described and widely practiced. In these processes a feed stream is contacted with a selective adsorbent which adsorbs the desired isomer. The desired isomer is then removed from the adsorbent by contacting it with a desorbent, forming an extract stream. Benzene, toluene, and p-diethylbenzene were described as suitable desorbents in the early references, with p-diethylbenzene (p-DEB) having become a commercial standard for this separation. P-DEB is a "heavy" desorbent (higher boiling than p-xylene) which allows for easier recovery of the desorbent from the other extract and raffinate components, mainly $C_8$ aromatics, by fractional distillation. Unfortunately p-DEB has a disadvantage when the feed stream contains $C_9$ aromatics, as is often the case when the feedstock is derived from a crystallizer. This problem is the result of the boiling point of p-DEB being very close to the boiling point of $C_9$ aromatics in the feed. Because the $C_9$ aromatics are difficult to separate from p-DEB by simple fractionation, the $C_9$ aromatics gradually build up in the desorbent, which must be reused in any economically feasible commercial process.

It has been therefore been necessary in the commercial processes for adsorptive separation of p-xylene from feed mixtures containing the other xylene isomers to reduce the $C_9$ aromatics content of the feed stream to less than about 0.1% prior to passing the feed stream into the adsorptive separation zone. This is usually done by distillation in a so-called xylene splitter column. The very substantial costs associated with this practice, such as the capital costs of the xylene splitter and the utilities cost of the fuel and energy necessary to achieve substantially complete removal of the $C_9$ aromatics, can be eliminated if it is not necessary to first remove the $C_9$ aromatics. It is an objective of the subject invention to provide a "heavy" desorbent for paraxylene adsorptive separation processes. It is a specific objective of the subject invention to provide a process which allows the adsorptive recovery of para xylene from a feed stream comprising $C_9$ aromatic hydrocarbons without requiring extensive prefractionation of the feed stream to remove $C_9$ aromatics.

I have discovered a novel heavy desorbent for the adsorptive separation of p-xylene from its isomers employing a zeolitic adsorbent. This discovery is the unexpectedly superior performance of 1,4 diisopropylbenzene (1,4 DIPB) as a heavy desorbent.

During the adsorption step of the subject process a feed mixture containing a mixture of xylene isomers, preferably including para-xylene, and $C_9$ aromatics is contacted with the adsorbent at adsorption conditions and the desired xylene is selectively adsorbed and retained by the adsorbent while the other components of the feed mixture such as ethylbenzene are relatively unabsorbed. The adsorbent containing the more selectively adsorbed desired xylene is referred to as a "rich" adsorbent; that is, containing a near equilibrium loading of the more selectively adsorbed xylene. The unabsorbed raffinate components of the feed mixture are then removed from the interstitial void spaces between the particles of adsorbent and from the surface of the adsorbent. The adsorbed xylene is then recovered from the rich adsorbent by contacting the rich adsorbent with a single stream comprising a desorbent material at desorption conditions. The desorbent displaces the desired xylene to form a single extract stream which is transferred to a fractionation zone for recovery of the desired xylene. In the subject process only the desired xylene isomer is retained on the adsorbent and substantially all ethyl benzene present in the feed stream is removed in the raffinate stream. The single extract stream is therefore substantially free (contains less than 10 mole %) of ethylbenzene.

The subject invention can be practiced in a fixed or a moving adsorbent bed systems, but the preferred system for this separation is a countercurrent simulated moving bed system, such as described in U.S. Pat. No. 2,985,589, incorporated herein by reference for its teaching in the practice of simulated moving bed (SMB) adsorptive separation processes. Cyclic advancement of the input and output streams of this simulation can be accomplished by a multiple valve manifold system or by rotary disc valves as shown in U.S. Pat. Nos. 3,040,777 and 3,422,848. In these simulated moving bed systems the adsorbent is divided between eight or more subbeds. Equipment utilizing these SMB principles can vary in size from the pilot plant scale shown in U.S. Pat. No. 3,706,812 to commercial scale, with flow rates ranging from a few cc per hour to many thousands of gallons per hour. The invention may also be practiced in a cocurrent, pulsed batch process, like that described in U.S. Pat. No. 4,159,284 or in a cocurrent, continuous process, like that disclosed in U.S. Pat. Nos. 4,402,832 and 4,478,721.

The functions and properties of adsorbents and desorbents in the chromatographic separation of liquid components are well-known, and reference may be made to U.S. Pat. No. 4,642,397, which is incorporated herein, for additional description of these adsorption fundamentals.

Adsorbents to be used in the process of this invention comprise the specific crystalline aluminosilicates molecular sieves classified as X and Y zeolites. X zeolites, specifically X zeolites exchanged with barium or barium and potassium ions at their exchangeable sites, are the preferred adsorbents. These zeolites have known cage structures in which the alumina and silica tetrahedra are intimately connected in an open three-dimensional network to form cage-like structures with window-like pores. The tetrahedra are cross-linked by the sharing of oxygen atoms with spaces between the tetrahedra occupied by water molecules prior to partial or total dehydration of the zeolite. Dehydration of the zeolite results in crystals interlaced with cells having molecular dimensions and thus the crystalline aluminosilicates are often referred to as "molecular sieves" when the separation which they effect is dependent essentially upon differences between the sizes of the feed molecules as, for instance, when smaller normal paraffin molecules are separated from larger isoparaffin molecules by using a particular molecular sieve. In the process of this invention, however, the term "molecular sieves" is not strictly suitable since the separation of specific aromatic isomers is apparently highly dependent on differences in electrochemical attraction of the different isomers and the adsorbent rather than on purely physical size differences in the isomer molecules.

In a hydrated form, the type X aluminosilicate zeolites are represented by the formula below in terms of moles of oxides:

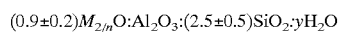

where "M" is a cation having a valence of not more than 3 which balances the electrovalence of the tetrahedra and is generally referred to as an exchangeable cationic site, "n" represents the valence of the cation, and "y", which represents the moles of water, is a value up to about 9 depending upon the identity of "M" and the degree of hydration of the crystal. As noted from Formula 1, the $SiO_2/Al_2O_3$ mole ratio is 2.5±0.5. The cation "M" may be monovalent, divalent or trivalent cations or mixtures thereof. In the separation of the invention, "M" is barium or a mixture of barium and potassium.

Crystalline aluminosilicates or zeolites are used in adsorption separations in the form of particle agglomerates having high physical strength and attrition resistance. The agglomerates used in separative processes contain the crystalline material dispersed in an amorphous, inorganic matrix or binder, having channels and cavities therein which enable liquid access to the crystalline material. Methods for forming the crystalline powders into such agglomerates include forming a wet mixture of an inorganic binder, generally a clay comprising a silicon dioxide and aluminum oxide, to high purity zeolite powder. The binder aids in forming or agglomerating the crystalline particles which otherwise would comprise a fine powder. The blended clay-zeolite mixture is extruded into cylindrical pellets or formed into beads which are subsequently calcined in order to convert the clay to an amorphous binder of considerable mechanical strength. The adsorbent particles may thus be in the form of extrudates, tablets, macrospheres or granules having a desired particle range, preferably from about 16 to about 60 mesh (Standard U.S. Mesh) (1.9 mm to 250 microns). Clays of the kaolin type, water permeable organic polymers or silica are generally used as binders.

Those skilled in the art will appreciate that the performance of an adsorbent is greatly influenced by a number of factors not related to its composition such as operating conditions, feed stream composition, water content and desorbent composition. The optimum adsorbent composition is therefore dependent upon a number of interrelated variables. One such variable is the water content of the adsorbent which is expressed herein in terms of the recognized Loss on Ignition (LOI) test. In the LOI test the volatile matter content of the zeolitic adsorbent is determined by the weight difference obtained before and after drying a sample of the adsorbent at 500° C. under an inert gas purge such as nitrogen for a period of time sufficient to achieve a constant weight. It is preferred that the water content of the adsorbent results in an LOI at 500° C. of less than 7.0%, more preferably within the range of from 0 to 6.5 wt % and most preferably from 3.0 to 6.5 wt. %.

The zeolite will ordinarily be present in the adsorbent particles as small crystals in amounts ranging from about 75 to about 98 wt. % of the particle based on volatile-free composition. Volatile-free compositions are generally determined after the adsorbent has been calcined at 900° C. in order to drive off all volatile matter. The remainder of the adsorbent will generally be the inorganic matrix present in intimate mixture with the small particles of the zeolite material. This matrix material may be an adjunct of the manufacturing process for the zeolite (for example, from the intentionally incomplete purification of the zeolite during its manufacture) or it may be added to relatively pure zeolite, but in either case its usual purpose is as a binder to aid in forming or agglomerating the zeolite into the hard particles.

In the present invention the separation of a xylene isomer is effected by passing a feed mixture comprising two or three isomers over a bed of an adsorbent which selectively adsorbs the desired xylene while permitting other components of the feed stream to pass through the adsorption zone in an unchanged condition. The flow of the feed is stopped and the adsorption zone is then flushed to remove nonadsorbed materials surrounding the adsorbent. Thereafter the desired xylene is desorbed from the adsorbent by passing a desorbent stream through the adsorbent bed, with the desorbent material comprising an aromatic hydrocarbon described herein. The desorbent material is commonly also used to flush nonadsorbed materials from the void spaces around and within the adsorbent. In the subject process only a single desorbent stream is employed. The composition, temperature and strength of the desorbent stream preferably remain constant during the desorption step, but can vary slightly due to the cyclic nature of the composition of raffinate and extract streams.

For purposes of this invention, various terms used herein are defined as follows. A "feed mixture" is a mixture containing one or more extract components and one or more raffinate components to be separated by the process. The term "feed stream" indicates a stream of a feed mixture which passes to the adsorbent used in the process. An "extract component" is a compound or class of compounds that is more selectively adsorbed by the adsorbent while a "raffinate component" is a compound or type of compound that is less selectively adsorbed. The term "desorbent material" shall mean generally a material capable of desorbing an extract component from the adsorbent. The term "raffinate stream" or "raffinate output stream" means a stream in which a raffinate component is removed from the adsorbent bed. The composition of the raffinate stream can vary from essentially 100% desorbent material to essentially 100% raffinate components. The term "extract stream" or "extract output stream" shall mean a stream in which an extract material which has been desorbed by a desorbent material is removed from the adsorbent bed. The composition of the extract stream, likewise, can vary from essentially 100% desorbent material to essentially 100% extract components. At least portions of the extract stream and the raffinate stream are passed to separation means, typically fractional distillation columns, where at least a portion of desorbent material is recovered to produce an extract product and a raffinate product. The terms "extract product" and "raffinate product" mean products produced by the process containing, respectively, an extract component and a raffinate component in higher concentrations than those found in the extract stream and the raffinate stream. The term "rich" is intended to indicate a concentration of the indicated compound or class of compounds greater than 50 mole percent.

The rate of exchange of an extract component with the desorbent can generally be characterized by the width of the peak envelopes at half intensity obtained from plotting the composition of various species in the adsorption zone effluent during a pulse test versus time. The narrower the peak width, the faster the desorption rate. The rate of exchange of various components can be expressed as "stage time" which is calculated from the net retention volume and the half width peaks of the components according to the formula in *Principles of Adsorption and Adsorption Processes* by Douglas M. Ruthven, published by John Wiley & Sons, 1984. The desorption rate can also be characterized by the distance between the center of a tracer peak envelope and the disappearance of an extract component which has just been desorbed. This distance is the volume of desorbent pumped during this time interval.

Selectivity, $(\beta)$, for an extract component with respect to a raffinate component may be characterized by the ratio of the distance between the center of the extract component peak envelope and the tracer peak envelope (or other reference point) to the corresponding distance between the center of the raffinate component peak envelope and the tracer peak envelope.

Relative selectivity can be expressed not only for one feed compound as compared to another but can also be expressed between any feed mixture component and the desorbent material. The selectivity, $(\beta)$, as used throughout this specification is defined as the ratio of the two components in the adsorbed phase divided by the ratio of the same two components in the unabsorbed phase at eouilibrium conditions. Relative selectivity is given by the equation:

$$\text{Selectivity} = \frac{\text{wt. percent } C/\text{wt. percent } D_A}{\text{wt. percent } C/\text{wt. percent } D_U}$$

where C and D are two components of the feed represented in weight percent and the subscripts A and U represent the adsorbed and unabsorbed phases, respectively. The equilibrium conditions are determined when the feed passing over a bed of adsorbent does not change composition, in other words, when there is no net transfer of material occurring between the unabsorbed and adsorbed phases.

Where selectivity of two components approaches 1.0, there is no preferential adsorption of one component by the adsorbent with respect to the other; they are both adsorbed to about the same degree with respect to each other. As β becomes less than or greater than 1.0, there is a preferential adsorption by the adsorbent for one component with respect to the other. When comparing the selectivity by the adsorbent of component C over component D, a β larger than 1.0 indicates preferential adsorption of component C within the adsorbent. A β less than 1.0 would indicate that component D is preferentially adsorbed leaving an unabsorbed phase richer in component C and an adsorbed phase richer in component D.

While separation of an extract component from a raffinate component is theoretically possible when the selectivity of the adsorbent for the extract component with respect to the raffinate component is not much greater than 1, it is preferred that such selectivity approach a value of 2. Analogous to relative volatility in fractional distillation, the higher the selectivity, the easier the adsorptive separation is to perform. Higher selectivities permit a smaller amount of adsorbent to be used.

The "speed" of the adsorption steps at various conditions or for different adsorbent/desorbent combinations can be measured and compared as stage times. Stage times are normally inversely correlated with temperature. That is, as the temperature goes up, the stage times normally go down. A higher temperature is therefore normally desired since low stage times mean a smaller, less expensive plant is required to separate a given quantity of feed material. On the other hand selectivity is normally negatively impacted by higher temperatures. That is, selectivity normally decreases as the temperature goes up. In designing a commercial scale separation unit of this type, it is therefore necessary to choose operating conditions based upon a balance or trade-off of stage times versus selectivity.

An important characteristic of an adsorbent is the rate of exchange of the desorbent for the extract component of the feed mixture materials or, in other words, the relative rate of desorption of the extract component. This characteristic relates directly to the amount of desorbent material that must be employed in the process to recover the extract component from the adsorbent. Faster rates of exchange reduce the amount of desorbent material needed to remove the extract component, and therefore, permit a reduction in the operating cost of the process. With faster rates of exchange, less desorbent material has to be pumped through the process and separated from the extract stream for reuse in the process. Ideally, desorbent materials should have a selectivity equal to about 1 or slightly less than 1 with respect to all extract components so that all of the extract components can be desorbed as a class with reasonable flow rates of desorbent material, and so that extract components can displace desorbent material in a subsequent adsorption step.

In adsorptive separation processes, which are generally operated continuously at substantially constant pressures and temperatures to insure liquid phase, the desorbent material must be judiciously selected to satisfy many criteria. First, the desorbent material should displace an extract component from the adsorbent with reasonable mass flow rates without itself being so strongly adsorbed as to unduly prevent an extract component from displacing the desorbent material in a following adsorption cycle. Expressed in terms of the selectivity, it is preferred that the adsorbent be more selective for all of the extract components with respect to a raffinate component than it is for the desorbent material with respect to a raffinate component. Secondly, desorbent materials must be compatible with the particular adsorbent and the particular feed mixture. More specifically, they must not reduce or destroy the capacity of the adsorbent or selectivity of the adsorbent for an extract component with respect to a raffinate component. Additionally, desorbent materials should not chemically react with or cause a chemical reaction of either an extract component or a raffinate component. Both the extract stream and the raffinate stream are typically removed from the adsorbent void volume in admixture with desorbent material and any chemical reaction involving a desorbent material and an extract component or a raffinate component or both would complicate or prevent product recovery. Finally, desorbent materials should be readily available and reasonable in cost, which is a problem with some prior art "heavy" desorbents.

The desorbent material of the subject invention is 1,4 (para) diisopropylbenzene which has a boiling point of 210° C. compared to the 184° C. boiling point of p-diethylbenzene. This allows easy separation from the $C_9$ aromatics. The preferred desorbent material is essentially free (contains less than 15 mole %) of any diluents such as paraffinic hydrocarbons. In a commercial situation the preferred desorbent material may contain small amounts of other diisopropylbenzene isomers but still preferably contains less than 10 mole % 1,3 DIPB and most preferably is composed of at least 90% 1,4 DIPB.

Feed mixtures which can be utilized in the process of this invention comprise para-xylene and at least one other $C_8$ aromatic isomer, and may also contain one or more $C_9$ aromatics as impurities. Thus, the feed mixtures to the process of this invention can contain sizable quantities of $C_9$ aromatics and may also contain quantities of straight or branched chain paraffins, cycloparaffns, or olefinic material having boiling points relatively close to the desired xylene isomer. It is preferable to have these quantities at a minimum amount in order to prevent contamination of products from this process by materials which are not selectively adsorbed or separated by the adsorbent. Preferably, the above-mentioned contaminants should be less than about 20% of the volume of the feed mixture passed into the process.

Feed mixtures for the process of this invention may be obtained from isomerization and transalkylation processes. For instance, the transalkylation of mixtures of $C_7$ and $C_9$ aromatics produces xylene isomers. Xylene mixtures which are deficient in one or more isomers, such as the raffmate of the subject process, can be isomerized, at isomerization conditions, to produce an effluent containing $C_8$ aromatic isomers, e.g., enriched in p-xylene, as well as $C_8$ non-aromatics and $C_9$ aromatics. The $C_9$ aromatic content of isomerized xylene isomers can be as much as 1–2 wt. % depending on isomerization conditions.

Mixtures containing substantial quantities of para-xylene and other $C_8$ aromatic isomers and $C_9$ aromatics generally are also produced by catalytic naphtha reforming and/ aromatic hydrocarbon isomerization processes, processes which are well known in the refining and petrochemical arts. In catalytic naphtha reforming processes, a naphtha boiling range feed is contacted with a platinum and halogen-containing catalyst at severities selected to produce an effluent containing $C_8$ aromatic isomers. Generally, the reformate is then fractionated to concentrate the $C_8$ aromatic isomers into a $C_8$ fraction which will also contain $C_8$ nonaromatics and some $C_9$ aromatics. Many $C_9$ aromatics have boiling points in the range of 160°–170° C. and cannot be easily removed by distillation from the prior art p-diethylbenzene desorbent.

These mixed component feeds therefore require either a xylene splitter column to remove the $C_9$ aromatics from $C_8$ aromatics or a heavy desorbent in order to obtain economic commercial scale operation. The use of a heavy desorbent is the more economically attractive choice. I have discovered a suitable desorbent which can be easily separated from the $C_9$ aromatics by fractionation and therefore does not require this large fractionation column and the associated utilities costs needed to pretreat the feed, resulting in substantial cost savings.

Adsorption conditions in the subject process include a temperature range of from about 20° to about 250° C., with about 60° to about 200° C. being more preferred, and a pressure sufficient to maintain liquid phase, which may be from about atmospheric to 600 psig. Desorption conditions include the same range of temperatures and pressure as used for adsorption conditions. Specifically the adsorption and desorption steps are preferably performed at substantially the same temperature and pressure. Further the temperature is preferably not varied between or within beds of adsorbent. The temperature is therefore uniform and constant throughout the adsorbent chamber(s) during the process.

A dynamic testing apparatus may be employed to test adsorbents and desorbent materials with a particular feed mixture to measure the adsorbent characteristics of adsorptive capacity and exchange rate. This "pulse test" apparatus consists of a helical adsorbent chamber of approximately 70 cc volume having inlet and outlet portions at opposite ends of the chamber. The tubular chamber is contained within a temperature control means and, in addition, pressure control equipment is used to operate the chamber at a constant predetermined pressure. Quantitative and qualitative analytical equipment, such as refractometers, polarimeters, chromatographs, etc., can be attached to the outlet line of the chamber and used to analyze the effluent stream leaving the adsorbent chamber.

During a pulse test the following general procedure is used to obtain data; e.g., selectivities, for various adsorbent/desorbent systems. The adsorbent is filled to equilibrium with a particular desorbent by passing the desorbent material through the adsorbent chamber. At a convenient time, a pulse of feed containing known concentrations of a tracer and of a particular extract component or of a raffinate component, or both, all diluted in desorbent material is injected for a duration of several minutes. Desorbent flow is resumed, and the tracer and the extract and raffinate components are eluted as in a liquid-solid chromatographic operation. The effluent can be analyzed by on-stream chromatographic equipment and traces of the envelopes of corresponding component peaks developed. Alternatively, effluent samples can be collected periodically and later analyzed separately as by gas chromatography.

From information derived from the test, adsorbent/desorbent system performance can be rated in terms of void volume, retention volume for an extract or a raffinate component, and the rate of desorption of an extract component from the adsorbent and selectivity. Void volume is the non-selective volume of the adsorbent, which is expressed by the amount of desorbent pumped during the interval from initial flow to the center of the peak envelope of the tracer. The net retention volume of an extract or a raffinate component may be characterized by the distance between the center of the peak envelope (gross retention volume) of the extract or raffinate component and the center of the peak envelope (void volume) of the tracer component or some other known reference point. It is expressed in terms of the volume in cubic centimeters of desorbent material pumped during this time interval represented by the distance between the peak envelopes. The rate of exchange or desorption rate of an extract component with the desorbent material can generally be characterized by the width of the peak envelopes at half intensity. The narrower the peak width, the faster the desorption rate. The desorption rate can also be characterized by the distance between the center of the tracer peak envelope and the disappearance of an extract component which has just been desorbed. This distance is again the volume of desorbent material pumped during this time interval. Selectivity, $\beta$, can be determined by the ratio of the net retention volumes of the more strongly adsorbed component to each of the other components.

One embodiment of the subject process may be characterized as a continuous simulated moving bed process for the adsorptive separation of a desired first xylene isomer from a feed mixture comprising $C_9$ aromatic hydrocarbons and at least one other xylene isomer which process comprises contacting said feed mixture with an adsorbent comprising an X zeolite containing barium or barium and potassium ions at exchangeable cationic sites at adsorption conditions and effecting the selective adsorption of the desired xylene isomer by said adsorbent and the production of a raffinate stream comprising said other xylene isomer; and subsequently contacting said adsorbent with a single desorbent stream comprising 1,4 diisopropylbenzene at desorption conditions which include a substantially constant and uniform temperature equal to the temperature of the adsorption conditions to effect the removal of the desired xylene isomer from said adsorbent as an extract stream and recovering the desired xylene isomer.

It may appear relatively simple to pick suitable heavy desorbents for this process using tables of physical characteristics, such as boiling points, for light aromatics. However, it has been found that this is not the case and that considerable testing is required to find suitable desorbents. A difference of one carbon atom on any alkyl group can make a significant difference in a compound's performance as a desorbent. This is further complicated by the sensitivity of the adsorption and desorption steps to numerous variables including the identity of the molecular sieve, the hydration level of the sieve, the temperature imposed on the system, the specific cations and level of cation exchange of the zeolitic molecular sieves. The data present below demonstrates the unpredictability in this area and the relative utility of different diisopropylbenzenes as desorbents for this process. The following non-limiting examples are also presented to illustrate the process of the present invention and are not intended to unduly restrict the scope of the claims attached hereto.

EXAMPLES

The experiments reported below summarize a number of pulse tests, using the apparatus as described above, to evaluate the ability of different adsorbent/desorbent combinations to separate paraxylene (b.p. 138° C.) from the other xylene isomers and ethylbenzene (b.p.'s from 136°–145° C.) and from $C_9$ aromatics. The three adsorbents used were an X zeolite exchanged with barium or barium and potassium and a Y zeolite having potassium loaded onto its exchangeable sites. Both adsorbents comprised a similar amorphous clay binder.

For each pulse test, the column was maintained at the indicated constant temperature and at a pressure of approximately 165 psig to maintain liquid-phase operations. Gas chromatographic analysis equipment was attached to the column effluent stream to determine the composition of the effluent material at given time intervals. The feed mixture employed for each test was a mixture containing 20 vol. percent of each of the xylene isomers, ethylbenzene and normal nonane used as a tracer. The desorbents were in some instances diluted with heptane to increase the retention time in order to make the results more precise. The compositions of the desorbents are given in Table 1. The operations performed during a test were as follows: The desorbent material was run continuously through the test apparatus at a rate of about 1.33 cc per minute. At some convenient time, the desorbent was stopped and the feed mixture was injected into the column over a 3.8 minute interval. The flow of the desorbent stream was then resumed and continued through the adsorbent column until all of the feed aromatics had been eluted from the column as determined by chromatographic analysis of the effluent material leaving the adsorption column.

TABLE 1

DESORBENT COMPOSITIONS

| | Boiling pt °C. | vol. % | |
|---|---|---|---|
| A | 293 | 30/70 | phenyldecane/n-heptane |
| B | 264.5 | 30/70 | diphenylmethane/n-heptane |
| C | 210 | 30/70 | 1,4-diisopropylbenzene/n-heptane |
| D | 237 | 30/70 | 1,4-ditertiarybutylbenzene/n-heptane |
| E | 203 | 100 | 1,3-diisopropylbenzene |
| F | 216 | 30/70 | 1,3,5-triethylbenzene/n-heptane |
| G | 205 | 30/70 | 5-tertiarybutyl-m-xylene/n-heptane |

Table 2 lists the net retention volume (NRV) for paraxylene, the stage time and the selectivity, β, for ethylbenzene, orthoxylene and metaxylene with respect to the reference p-xylene. The table also lists the adsorbent used in each test, the hydration of the adsorbent by LOI and the temperature at which the test was run.

An examination of the data given in Table 2 shows the surprising and unexpected interaction between the members of the adsorbent/desorbent system and the effect on xylene separation performance. For instance, run 8273-1 using potassium exchanged Y-zeolite and 1,4 diisopropylbenzene as the desorbent shows no desorption of paraxylene during the desorption step while run 8026-96 using the same zeolite with 1,4 ditertiarybutylbenzene shows good selectivities but somewhat higher than desired N.R.V. and stage time. This illustrates a difference of one carbon on the alkyl group can have a tremendous effect on system performance.

Another example of how system performance is dependent on the desorbent is the comparison of runs 8019-86, 8019-64 and 8026-89 which all use the same barium exchanged X zeolite sieve at similar hydration levels and the same temperature of 200° C. The data shows desorbent C (1,4 diisopropylbenzene) to be much superior in terms of a lower retention volume and stage time compared to desorbent A (phenyldecane) and desorbent G (5-tertiarybutyl-m-xylene). Therefore desorbents are not interchangeable unless different process performance is acceptable. Second, no basis exists at this time to predict this relative performance.

A second example of this is seen in comparing runs 8273-1 and 8026-100. In this comparison the adsorbent comprises KY zeolite, the temperature is 200° C. and the LOI is 0. Only the desorbent is changed with run 8273-1 using the subject 1,4 DIPB and run 8026-100 using 1,3,5 triethylbenzene. The results of the tests were "no desorption of PX" in run 8273-1 but reportable results for run 8026-100 thus again showing the composition of the desorbent is critical for successful operation of the process.

The performance of an adsorbent/desorbent pair is also dependent on the adsorbent. A comparison of runs 8026-99, 8026-98 and 8273-4 shows the surprising result that desorbent B (diphenylmethane) gives good performance with a potassium Y sieve but no separation with a barium X sieve.

The performance of 1,4 and 1,3 diisopropylbenzene may be directly compared by reviewing the results of runs 8019-79 and 8019-60. Both of these runs were performed using an adsorbent comprising barium-exchanged zeolite X

TABLE 2

| Run No. | LOI @ 500° C. | Adsorbent | Temp (°C.) | Desorbent | N.R.V. p-xylene (ml.) | p-x selectivity EB | MX | OX | stage time (sec.) |
|---|---|---|---|---|---|---|---|---|---|
| 8019-86 | 6.5 | BaX | 200 | A | 107 | 1.84 | 3.02 | 2.83 | 22.2 |
| 8019-87 | 0.5 | KY | 177 | A | (no desorption of PX) | | | | |
| 8026-99 | 0 | BaX | 200 | B | (no separation) | | | | |
| 8026-98 | 0 | KY | 200 | B | 10.5 | 1.68 | 3.08 | 1.89 | 29.7 |
| 8273-4 | 0 | KY | 145 | B | 13.9 | 1.73 | 2.50 | 2.16 | 27.6 |
| 8019-79 | 4.1 | BaX | 200 | C | 56.4 | 2.28 | 3.45 | 3.34 | 19.8 |
| 8019-64 | 5.0 | BaX | 200 | C | 37.5 | 1.90 | 2.58 | 2.46 | 18.7 |
| 8273-1 | 0 | KYX | 200 | C | (no desorption of PX) | | | | |
| 8273-2 | 0 | BaK | 200 | C | (no separation) | | | | |
| 8026-95 | 0 | BaX | 185 | D | (no desorption of all $C_8$) | | | | |
| 8026-94 | 0.2 | BaKX | 185 | D | (no desorption of all $C_8$) | | | | |
| 8026-96 | 0 | KY | 185 | D | 72 | 2.4 | 9.5 | 6.3 | 43.5 |
| 8019-60 | 4.1 | BaX | 200 | E | 52.7 | 2.3 | 3.79 | 3.41 | 23.5 |
| 8026-100 | 0 | KY | 200 | F | 61.4 | 2.33 | 7.58 | 5.23 | 40.8 |
| 8026-93 | 4.7 | BaX | 200 | F | 77.6 | 1.3 | 3.0 | 2.32 | 43.9 |
| 8026-84 | 0.2 | BaKX | 195 | G | (no separation) | | | | |
| 8026-89 | 5.6 | BaX | 200 | G | 73.2 | 1.94 | 3.28 | 2.87 | 23.4 |
| 8026-89 | 0.1 | KY | 200 | G | 62.9 | 2.37 | 4.37 | 3.82 | 15.4 |
| 8026-87 | 4.2 | KY | 200 | G | 47.0 | 1.97 | 3.65 | 3.25 | 21.3 |
| 8026-88 | 4.7 | KY | 200 | G | 44.3 | 1.97 | 3.59 | 2.23 | 28.2 |
| 8026-89 | 5.7 | KY | 200 | G | 47.1 | 2.05 | 3.72 | 3.37 | 54.5 | having an LOI of 4.1 at a temperature of 200° C. The net retention volumes and selectivities for these two desorbents are similar, and stage time is slightly lower for desorbent C comprising the 1,4 diisopropylbenzene. This result shows that desorbent strength cannot be predicted on the basis of two isomers giving similar results since desorbent C was diluted to contain only 30% of the active compound while desorbent E was totally undiluted. Hence, 1,4 diisopropylbenzene is a surprisingly stronger desorbent than 1,3 diisopropylbenzene.

Because of this unexpected finding a further test was performed at the same conditions with the same adsorbent but with a desorbent of 100% 1,4 diisopropylbenzene. Stage times for the two desorbents were similar, with that for 100% 1,4 diisopropylbenzene being 26.7 seconds. The selectivity of 1,4 DIPB for ortho-xylene over para-xylene is 3.7 versus 3.4 for 1,3 DIPB thus indicating a higher selectivity and the ability to more readily reach any desired purity target. This test resulted in a paraxylene net retention volume of 22.6 vs. the 52.7 listed in Table 2 for 1,3 diisopropylbenzene.

More importantly, the difference in net retention volume again shows 1,4 diisopropylbenzene is a much stronger desorbent than 1,3 diisopropylbenzene. This, in turn, has very significant economic impact on a commercial adsorptive separation unit. It allows a corresponding reduction in desorbent usage and/or the size of the desorption zone (Zone III) of the adsorbent bed of a simulated moving bed system. Decreased desorbent rates reduce the required desorbent inventory, the required size of desorbent transfer lines, and the required size and operating costs of desorbent recovery fractionation columns, etc. The unexpectedly stronger desorbent properties of 1,4 DIPB over 1,3 DIPB thus translate into significant cost reductions in a commercial simulated moving bed adsorption process for para-xylene recovery.

What is claimed is:

1. In a continuous simulated moving bed process for the adsorptive separation of a desired first xylene isomer from a feed mixture comprising at least two isomers of xylene which process comprises contacting said feed mixture with an adsorbent comprising a zeolite having one or more metal ions at exchangeable cationic sites at adsorption conditions and effecting the selective adsorption of the desired xylene isomer by said adsorbent and the production of a raffinate stream comprising a second xylene isomer the improvement which comprises using an adsorbent having an LOI at 500° C. of 3.0–6.5 wt. % and comprising a barium exchanged X zeolite, subsequently contacting said adsorbent with a single desorbent stream comprising 1,4 diisopropylbenzene at desorption conditions including a substantially constant temperature to effect the removal of the desired xylene isomer from said adsorbent as an extract stream, and recovering the desired xylene isomer, with the adsorption and desorption conditions including the same constant temperature.

2. A continuous simulated moving bed process for the adsorptive separation of a desired first xylene isomer from a feed mixture comprising at least two isomers of xylene which process comprises contacting said feed mixture with an adsorbent comprising an X zeolite having one or more metal ions at exchangeable cationic sites at adsorption conditions and effecting the selective adsorption of the desired xylene isomer by said adsorbent and the production of a raffinate stream comprising a second xylene isomer and substantially all ethylbenzene present in the feed stream; and subsequently contacting said adsorbent with a desorbent comprising 1,4 diisopropylbenzene at desorption conditions including a substantially constant temperature to effect the removal of the desired xylene isomer from said adsorbent as an extract stream, and recovering the desired xylene isomer, with the adsorption and desorption conditions including the same constant temperature.

3. The process of claim 2 wherein the feed mixture additionally comprises $C_9$ aromatic hydrocarbons.

4. The process of claim 3 wherein the adsorbent is an X zeolite having only barium at said exchangeable sites.

5. The process of claim 2 wherein the desorbent contains less than 10 mole % 1,3 diisopropylbenzene.

6. A continuous simulated moving bed process for the adsorptive separation of p-xylene from a feed mixture comprising $C_9$ aromatic hydrocarbons, p-xylene and at least one other isomer of xylene which process comprises contacting said feed mixture with a bed of an adsorbent having an LOI at 500° C. of 3.0–6.5 wt. % and comprising an X zeolite containing barium ions at exchangeable cationic sites at adsorption conditions and effecting the selective adsorption of p-xylene by said adsorbent and the production of a raffinate stream comprising said other xylene isomers; and subsequently contacting said bed of adsorbent with a single desorbent stream comprising 1,4 diisopropylbenzene at desorption conditions which include a substantially constant temperature equal to the temperature of the adsorption conditions to effect the removal of p-xylene from said adsorbent as an extract stream, and recovering the p-xylene.

7. The process of claim 6 wherein the desorbent contains less than 10 mole % 1,3 diisopropylbenzene.

8. The process of claim 6 wherein the desorbent is essentially free of paraffinic diluents.

\* \* \* \* \*